(12) United States Patent
Van Der Meijden et al.

(10) Patent No.: US 8,802,395 B2
(45) Date of Patent: Aug. 12, 2014

(54) METHOD FOR PROTEIN ISOLATION IN ANOXIC CONDITIONS

(75) Inventors: Peter Van Der Meijden, Oss (NL); Gijsbert Willem Karel Van Dedem, Oss (NL); Michel Hendrikus Maria Eppink, Oss (NL); Roeland Wilhelmus Wassenaar, Oss (NL)

(73) Assignee: MSD OSS B.V., Oss (NL)

( * ) Notice: Subject to any disclaimer, the term of this patent is extended or adjusted under 35 U.S.C. 154(b) by 0 days.

(21) Appl. No.: 13/467,305

(22) Filed: May 9, 2012

(65) Prior Publication Data

US 2013/0150553 A1    Jun. 13, 2013

Related U.S. Application Data

(63) Continuation of application No. 10/543,524, filed as application No. PCT/EP2004/000953 on Jan. 29, 2004, now abandoned.

(30) Foreign Application Priority Data

Jan. 31, 2003 (EP) .................................. 03100208

(51) Int. Cl.
*C12P 21/02* (2006.01)

(52) U.S. Cl.
USPC ........ 435/69.1; 435/69.4; 435/69.7; 435/71.2

(58) Field of Classification Search
None
See application file for complete search history.

(56) References Cited

U.S. PATENT DOCUMENTS

| | | | | |
|---|---|---|---|---|
| 4,801,691 A | * | 1/1989 | Auer | ............................. 530/399 |
| 4,923,967 A | * | 5/1990 | Bobbitt et al. | ................. 530/351 |
| 5,464,756 A | * | 11/1995 | Henner et al. | ............... 435/69.1 |
| 5,593,860 A | | 1/1997 | Fischer | |
| 5,869,045 A | | 2/1999 | Hellstrom et al. | |
| 5,952,461 A | | 9/1999 | Kim et al. | |
| 6,001,604 A | | 12/1999 | Hartman et al. | |
| 6,150,134 A | | 11/2000 | Maertens et al. | |
| 6,875,589 B1 | | 4/2005 | Dorschug et al. | |
| 8,378,080 B2 | * | 2/2013 | Watts et al. | ................ 530/387.1 |

FOREIGN PATENT DOCUMENTS

| | | |
|---|---|---|
| EP | 0055945 A2 | 7/1982 |
| EP | 0379162 A2 | 7/1990 |
| EP | 0196056 B1 | 10/1991 |
| WO | WO 96/20724 | 7/1996 |
| WO | WO 99/33988 | 7/1999 |

OTHER PUBLICATIONS

Rozkov et al., Biotech. Bioengineer., Vo. 62, No. 6, Mar. 20, 1999, pp. 730-738.
Green et al., Proc. R. Soc. Lond. B, vol. 244, 1991, pp. 137-144.
Green et al., Mol. Microbial., vol. 8, 1993, pp. 61-68.
International Search Report, No. PCT/EP2004/000953, May 26, 2004.
XP002254289, R. Hermann: "Protein Folding," 1993.
Derwent Abstract of EP 0379162 A2, Jul. 1990.

* cited by examiner

*Primary Examiner* — Jeffrey Stucker
*Assistant Examiner* — Stephen Gucker

(57) ABSTRACT

The present invention relates to a method for the isolation of proteins that comprise disulfide bonds in their native conformation. Essentially, a method of the present invention makes use of reducing agents such as β-mercaptoethanol or dithiothreitol in protein isolation methods obsolete. A method of the present invention is particularly suitable for the isolation of precursor proteins such as proinsulin from recombinant cells.

5 Claims, 2 Drawing Sheets

METHOD FOR PROTEIN ISOLATION IN
ANOXIC CONDITIONS

This patent application is a continuation of U.S. application Ser. No. 10/543,524, filed Sep. 1, 2005, now abandoned, which was a national stage entry of International Patent Application PCT/EP2004/000953, filed Jan. 29, 2004.

FIELD OF THE INVENTION

The invention relates to a method for the isolation of proteins. More particularly, the present invention provides methods for the isolation of proteins that comprise disulfide-bonds in their native conformation.

BACKGROUND OF THE INVENTION

The human peptide hormone insulin controls blood glucose levels during feeding and fasting and acts via cell surface receptors of liver and adipose tissue cells. Besides controlling uptake, storage and production of glucose, insulin is also i.a. involved in the control of production and breakdown of lipids.

Deficiencies in the supply of insulin result in elevated blood glucose concentrations (hyperglycaemia) and, in chronic form, are revealed by the classic symptoms of diabetes mellitus (DM). Insulin is administered daily to patients suffering from DM.

Mature human insulin is a peptide that is comprised of an A (alpha) and a B (beta) chain, linked by 2 inter-chain disulfide bridges. A third disulfide bridge connects two residues of the A chain. In proinsulin, the biosynthetic precursor, the A and B chains, are connected to each other by the C peptide, which role is to aid in appropriate disulfide bridge formation between the A and B segments and to allow proper folding of the proinsulin molecule. In the last stage of maturation, proteolytic enzymes cleave at specific amino acid residues to release the C peptide thus forming the mature insulin.

Biosynthetic recombinant human insulin is presently i.a. manufactured as proinsulin-like polypeptides expressed in e.g. *E. coli* or yeast (see e.g. U.S. Pat. No. 5,598,860). In moat cases, proinsulin is produced as a fusion protein or recombinant hybrid, wherein the proinsulin is cross-linked via methionine residues to a heteroprotein, such as for instance human capper/zinc superoxide dismutase (hSOD). Normally, these hybrids accumulate in the recombinant cells as intracellular precipitated protein or inclusion bodies.

During manufacturing of recombinant proinsulin, the inclusion bodies, obtained by centrifugation after lysis of the cells, are washed with a detergent or a denaturant at a low concentration. Such treatment is repeated to increase the purity of the desired protein. In order to minimize intermolecular hydrophobic interaction, and formation of incorrect disulfide bonds, the washed inclusion bodies are dissolved in a denaturant, such as a urea or guanidine-HCl solution containing a reducing agent such as dithiothreitol (DTT) or 2-mercaptoethanol, and recovered by precipitation.

The hybrid is normally isolated and cleaved by cyanogen bromide (CNBr) in order to release the proinsulin polypeptide from the heteroprotein. The proinsulin, is further modified by oxidative sulfitolysis to proinsulin S-sulfonate (See e.g. EP 0 055 945 and EP 0 196 056). The proinsulin. S-sulfonate is then further purified and refolded to a native conformation under reducing conditions by using reducing agents such as dithiothreitol (DTT), 2-mercaptoethanol, etc. or a redox system such as glutathione. Conversion of the proinsulin to insulin, i.e. removal of the C peptide, is achieved by the combined action of trypsin and carboxypeptidase B. Finally insulin is purified through e.g. reverse-phase high performance liquid chromatography (RP-HPLC) and optionally crystallized.

During the complete isolation procedure, from lysis of the recombinant cells through to proper folding of the proinsulin, free thiol groups of the cysteine residues comprised in the (fusion) protein, may form incorrect or aspecific intra- or intermolecular disulfide bridges. This results in scrambled peptides and inactive hormones or in the formation of 'aggregates' of desired proteins and contaminating proteins (U.S. Pat. No. 6,150,484). Therefore, free thiol groups should either be blocked in order to prevent the formation of incorrect disulfide bridges or procedures should involve selectively cleaving of incorrect disulfide bonds.

Disulfide bond cleaving may i.a. be achieved by: a) modifying the cysteine residues into cysteic acid by cysteic acid oxidation or performic acid treatment; b) modifying the cysteine into S-sulfo-cysteine by sulfitolysis (R—S—S—R→2R—SO$_3^-$); c) reduction by means of certain reducing agents, such as phosphines or mercaptans (see e.g. EP 0 379 162).

However, preventing the incorrect disulfide bonds to form is preferred over the use of "oxido-shuffling" agents following protein isolation, and to achieve this, again several reducing agents, each as dithiotreitol (DTT), β-mercaptoethanol, cysteine, glutathione, E-mercaptoethylamine or thioglycollic acid, are moat commonly used.

The use of all above-mentioned reducing agents, however, poses problems in that they pose a toxic risk in that they are costly, and in that their contamination of the product requires additional purification.

Therefore, the conventional process for preparing recombinant proinsulin is proven to be less satisfactory since it involves complicated steps of dissolution and sulfonation, purification, concentration, wherein the refolding of the proinsulin progresses inefficiently resulting in reduced yields of the desired protein.

Accordingly, there is a need for an improved process for the isolation of proteins which comprise disulfide-bonds in their native conformation in an efficient and less contaminating manner.

SUMMARY OF THE INVENTION

The present inventors have now found that the use of reducing agents in the isolation of proteins comprising disulfide bonds can be avoided or at least substantially reduced by performing said isolation under an essentially anoxic atmosphere.

The present invention provides a method for the isolation of proteins that comprise disulfide-bonds in their native conformation, said method comprising isolating said protein under essentially anoxic conditions.

By using the method of the present invention, disulfide-bonds comprising proteins can now be extracted and isolated from the environment without the need for the use of objectionable reducing agents. One of the advantages of the method of the present invention is that no extraction of such reducing agents from the isolated, and purified protein product is necessary any more and that thus the isolation procedure is more efficient. Moreover, a method of the invention prevents the formation of scrambled conformations of proteins and results in a high yield of proteins in their stable, native conformation.

DETAILED DESCRIPTION OF THE INVENTION

Figure 1:
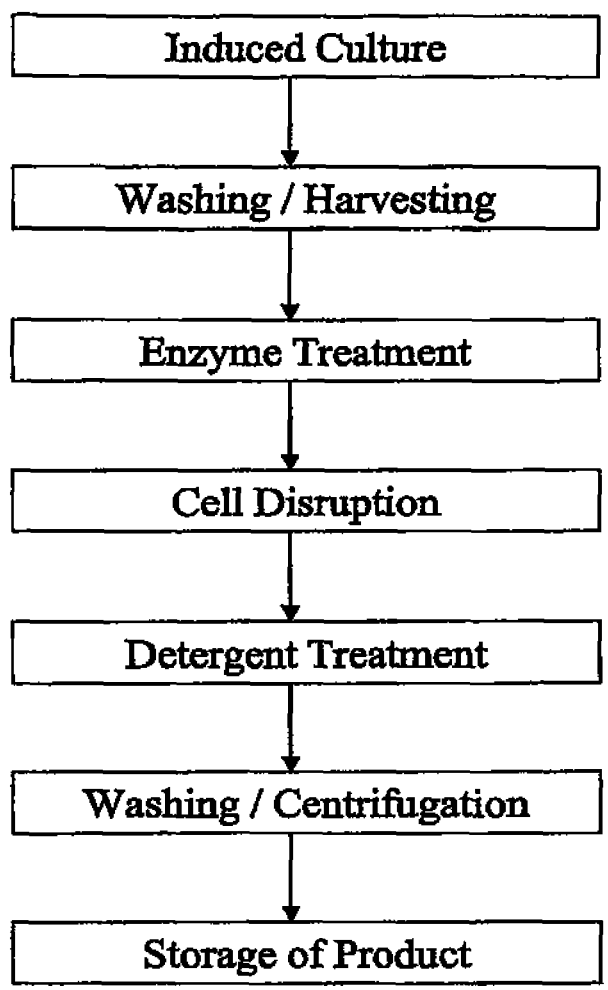
FIG. 1 is a schematic flow chart of the major procedural steps comprised in a method of the invention.

The term "purification" or "purifying" and "isolation" and "isolating" as used herein is defined as the process of releasing and obtaining a single constituent, such as a defined macromolecular species, from a mixture of constituents, such as from a culture of recombinant cells. In particular, an isolation procedure herein involves the harvest and lysis of cells, the extraction of particular proteins from a crude cell extract obtained from said lysis and may further comprise the various steps of isolating subcellular structures such as inclusion bodies that comprise the desired proteins from other cellular components such as nucleic acids or polysaccharides. More in particular, a purification procedure herein involves the process of isolating a protein in a fairly pure form, i.e. freeing it from further impurities upon its isolation.

"Isolated" and "purified" refer to any molecule or compound that is separated from its natural environment and is from about 60% to about 99% free, preferably 80% to 99% free from other components with which it is naturally associated.

The term "recombinant" as used herein refers to a protein or nucleic acid construct, generated recombinantly or synthetically, e.g., in the case of a protein, through the translation of the RNA transcript of a particular vector- or plasmid-associated series of specified nucleic acid elements or of an expression cassette in a host cell. The term "recombinant" as used herein does not encompass the alteration of the cell or vector by naturally occurring events (e.g., spontaneous mutation, natural transformation/transduction/transposition) such as those occurring without deliberate human intervention.

By "host call" is meant a cell, which contains a vector or expression cassette and supports the replication and/or expression thereof. Hoot cells may be prokaryotic cells such as $E. coli$, or eukaryotic cells such as yeast, insect, amphibian, plant cells or mammalian cells. Preferably, host cells are bacterial or prokaryotic cells. A particularly preferred host cell for the production of insulin is an $E. coli$ host cell, preferably $E. coli$. strain S$\phi$783.

As used herein, "vector" includes reference to a nucleic acid used in transfection of a host cell and into which can be inserted a polynucleotide. Vectors are often replicons.

The term "protein" or "proteins" as used herein refers to a polypeptide or any portion thereof.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as the modifications known in the art, both naturally occurring and non-naturally occurring.

The term "recombinant protein" as used herein refers to (1) a polypeptide of semisynthetic or synthetic origin resulting from the expression of a combination of DNA molecules of different origin that are joined using recombinant DNA technologies; (2) a polypeptide of semisynthetic or synthetic origin that, by virtue of its origin or manipulation, is not associated with all or a portion of a protein with which it is associated in nature; (3) a polypeptide of semisynthetic or synthetic origin that is linked to a polypeptide other than that to which it is linked in nature; or (4) a polypeptide of semisynthetic or synthetic origin that does not occur in nature.

The terms "inclusion body" and "retractile body" refer to the intracellular aggregates resulting from the non-specific precipitation of individual proteins. The formation of inclusion bodies and refractile bodies is a frequent consequence of high-level protein production in the cytoplasma. They are formed through accumulation of folding intermediates rather than from the native or unfolded protein. Inclusion bodies or retractile bodies can be formed by any or all of the following reasons: heterologous nature of expressed polypeptides; high protein expression rate; relatively high amount of hydrophobic protein that aggregates intermolecularly as a result of non-covalent association; and chaperones like helper proteins either being absent or inadequately available.

The term "disulfide-bond" or "disulfide bonds" as used herein is defined as one, resp. more, cross-links between polypeptide chains or between parts of a polypeptide chain formed by the oxidation of cysteine residues. The resulting disulfide is called a cystine.

The term "essentially anoxic" as used herein is defined as greatly deficient or substantially lacking in oxygen and may range from a reduction in the level of oxygen that is normally encountered in air, to a fully oxygenless condition of e.g. an atmosphere, a liquid environment or a tissue.

"Protein conformation" refers to the characteristic 3-dimensional shape of a protein, including the secondary (helices, sheet), supersecondary (motifs), tertiary (domains) and quaternary (multimeric proteins) structure of the peptide chain.

The term "native conformation" as used herein refers to the characteristic state, formation, shape or structure of a protein in the biologically active form in a living system in which it is folded to a global minimum of Gibbs free energy as defined by C.B. Anfinsen (Nobel Lecture, Dec. 11, 1972).

"Refolding" refers to the in vitro process of transformation of a protein after full denaturation by reductive cleavage of its disulfide bonds into a protein of native conformation.

Proteins with disulfide-bonds are generally not found in the cytoplasm with the exception of the sulfhydryl oxidoreductases. However, proteins that are exported from the cytoplasm, such as for instance insulin and alkaline phosphatase, typically contain disulfide bonds. This is often attributed to the difference in reducing potential between the cytoplasm and the extracellular environment, whereby the presence of thioredoxin reductases in the cytoplasm is believed to constitute an important factor. Several studies have shown that both cellular activity and thioredoxin reductase activity is required to keep extracellular proteins, which would comprise oxidized disulfide bonds in their native conformation, in an inactive and reduced form within the cytoplasm (Derman at al., 1993. Science 262:1744-47; Derman and Beckwith. 1995. J. Bacteria 177:3764-70).

After lysis (or cell death or growth arrest due to substrate depletion) thioredoxin reductases are no longer capable of maintaining the cystein residues of proteins in reduced form and random folding of the protein starts with concomitant oxidation of cysteine residues into disulfide bonds. This process often results in aberrantly folded or scrambled proteins.

In order to obtain a pure extract of proteins in their native conformation which comprises the presence of disulfide bonds, such as for instance insulin, from recombinant material, a key step is in the formation of correct disulfide bonds.

Conventional methods for the isolation of a protein that comprises disulfide bonds in its native conformation rely on the presence of reducing agents. It has now been found that the application of anoxic conditions from the moment the reducing power of thioredoxine reductases diminishes until the moment that the protein can be stabilized or conditions for correct folding are provided, can effectively prevent the formation of scrambled proteins.

In a first aspect, the present invention provides a method for the isolation of proteins that comprise disulfide-bonds in their native conformation, comprising isolating said protein under an essentially anoxic atmosphere.

Using a method of the present invention will result in an isolated protein product that is essentially free of contaminating reducing agents as described above, and wherein a large and substantial part of the proteins are active and in the native conformational state and biologically active.

Suitable proteins that can be used in a method of the invention are essentially proteins that comprise disulfide-bonds in their native conformation, but also other peptides may be isolated by a method of the invention. Very suitable proteins are for instance peptide hormones such as insulin, vasopressin, somatostatin, octreotide, endothelin I, knottin-like proteins, enzymes such as ribonuclease, epitopes such as epitopes of the Cn2 scorpion toxin, conotoxin, and/or LDL receptor epitope modules.

In general, disulfide-rich proteins, peptides or fragments thereof, be it either from viruses, bacteria, fungi (including yeast), plants, animals or humans, are valuable for studying structure-activity relationships in e.g. drug design. Therefore, also to this field, of science, the possibilities of the present invention to more efficiently attain the native conformation of these proteins, has important benefits.

A method of the invention is suitable for the isolation of proteins from any source that comprise disulfide bonds in the native conformation, such as associated with a virus or a prion or produced by a prokaryotic organism, such as a bacterium, or produced by a eukaryotic organism, such as a yeast, a fungus, a plant, an animal, or a human cell. Preferably said protein is an extracellular protein that is in the reduced form or state when expressed in the cytosol of a cell of the producing organism and that attains its native conformation when in the oxidized state.

The skilled person is capable of determining whether a protein comprising disulfide bonds is (re)folded properly and in the native conformation. Such determinations may for instance comprise the measurement of the properly folded, oxidized and digested Lys-Arg-Insulin intermediate, by HPLC analysis.

A method of the present invention is used preferably for the isolation of recombinantly produced proteins that comprise disulfide-bonds in the native conformation. Recombinantly produced proteins can be either directly expressed or expressed as a fusion protein. Detection of the expressed protein is achieved by methods known in the art such as, for instance, radioimmunoassays, Western blotting techniques or immunoprecipitation.

The manner of producing or (bio)synthesizing a (recombinant) protein is of no relevance to the method of the present invention. Recombinant proteins may iii principle be prepared by any method known in the art, for example, by such methods as be used for the preparation of recombinant proteins, such as for example by recombinant yeast, more preferably by a recombinant bacterium, most preferably by a recombinant $E.$ $coli$ cell, such as for instance described in U.S. Pat. No. 5,593,860. In many, but not necessarily all instances, such methods will result in the formation of fusion proteins or hybrids. Therefore, a method of the present invention is very suitably used for the isolation of fusion proteins.

In another preferred embodiment, the method is used to isolate such proteins as can be produced in inclusion bodies. In a most preferred embodiment, the method of the invention is used for the isolation of insulin precursor protein comprised in inclusion bodies as produced by the recombinant $E.$ $coli$ strain Sϕ733 carrying and expressing the plasmid pDBAST-RAT-N71 (Bio-Technology General Ltd., Rehovot, Israel), which is derived from the pDBAST-LAT vector (see U.S. Pat. No. 6,001,604 or WO 86/20124).

The present method involves the performance of a conventional process for the isolation of proteins, whereby this process is essentially performed under anoxic conditions. In a method of the invention, the initial steps of harvesting, lysing and protein extraction are performed under anoxic conditions without the use of reducing agents described above.

A method of the invention comprises the isolation of a protein under essentially anoxic conditions. Preferably, anoxic conditions are attained by providing the isolation environment with an anoxic atmosphere, such as a nitrogen atmosphere, a carbon dioxide atmosphere, or an atmosphere of helium or another inert gas. Most preferably, an atmosphere of $N_2$ is used in a method of the invention to provide anoxic conditions during the isolation of proteins that comprise disulfide bonds in the native conformation.

Preferably, an anoxic condition as applied in a method of the present invention is a condition equal to an atmosphere containing between 0 and 1 vol. %, preferably between 0 and 0.5 vol. %, even more preferably between 0 and 0.05% of $O_2$, or a liquid in equilibrium with said atmosphere. In a most preferred embodiment, the anoxic condition is a condition equal to an atmosphere containing essentially 0 vol. % of $O_2$, or a liquid is equilibrium with said atmosphere.

In short, a method of the invention for isolating proteins that comprise disulfide-bonds in their native conformation, does not comprise the growth of cells and/or the production of the proteins themselves. However, a method of the invention is performed on protein-producing material, such as production cells containing proteins, from the start of harvesting of the cells, including the post-harvesting washing of the cells, through to the stabilization of the isolated proteins by freezing, e.g. by freezing of the isolated inclusion bodies.

More in particular, when the reducing potential in the cytosol of the cell diminishes, as a result of the decreased activity of the thioredoxin reductases, e.g. when the cells stop growing, e.g. during harvesting and post harvesting washings, the wile are preferably already brought under anoxic conditions. Anoxic conditions are preferably maintained throughout the process until the start of the refolding of the protein.

A method of the invention may suitably comprise such steps as cell lysis, for instance by enzymatic pre-Treatment, followed by disruption or fragmentation of the cells, e.g. by sonication, French pressure cell treatment or high shear mixing such as Ultra-Turrax® treatment, provided that said lysis is performed under anoxic conditions. A further step in a method of the invention may comprise the separation or isolation of the inclusion bodies from the cytosol, in case the desired protein is produced therein, under anoxic conditions. After this step it is possible to store the isolated inclusion bodies and to stabilize the proteins comprised therein, for example by freezing, e.g. at −20° C., or cooling, e.g. at 2-8° C. Further process steps in the isolation and purification of the protein are not necessarily performed under anoxic conditions.

After release from storage, or directly after the above isolation steps, the isolated and optionally further purified protein may be refolded to the native conformation. Generally, for disulfide bonds containing proteins such refolding is performed in a dilute solution in order to avoid non-native intermolecular disulfide bridge formation. A very appropriate method for refolding of insulin comprises the dissolution of the protein in a $NaHCO_a$ and EDTA containing buffer at pH 12.0, reducing the pH to 11.2, treatment with charcoal and filtering. The polypeptides are then folded by applying air to the solution to oxidize the disulfides.

For fusion products, subsequent digestion of the fusion protein with an appropriate proteolytic enzyme may be performed to release the desired recombinant protein. The method of the invention may further comprise the purification to substantial purity of proteins by standard techniques well known in the art, including detergent solubilization, selective precipitation with such substances as ammonium sulphate, column chromatography, immunopurification methods, affinity chromatography, and others. See, for instance, R. Scopes, Protein Purification: Principles and Practice, Springer-Verlag: New York (1982); Deutscher, Guide to Protein Purification, Academic Press (1990).

The invention will now be exemplified by the following, non-limiting examples.

EXAMPLES

Following fermentation the culture liquid is brought to anoxic circumstances by shutting the addition of pressurized air, removal of overpressure and flushing of the headspace above the culture and process liquids with nitrogen. Flushing area headspace with nitrogen is continued during all subsequent processing steps, which include the harvest and washing of cells, cell lysis, and additional treatments of the inclusion bodies. Nitrogen flushing is also applied to processing equipment such as vessels, holding tanks, and auxiliary equipment such as centrifuges, homogenizers, and filtration units. Nitrogen flushing is executed using fixed piping.

Example 1

Two identical 450 L scale cultures of the recombinant human insulin precursor producing production strain Sϕ733/pDBAST-RAT-N-7-1 were grown from contents of identical working cell bank ampoules. The course of the fermentations was followed and samples of both cultures were analysed using validated analytical procedures. The results demonstrate that both cultures proceeded in very comparable manner and that the obtained absorbance, dry weight, protein and relative insulin precursor final concentrations showed dissimilarities of 8% or less.

Following fermentation, both cultures were subjected to identical inclusion body (IB) recovery procedures, which is schematically shown in the flow chart of FIG. 1.

During the IB recovery procedure a blanket of nitrogen gas was applied only to the latter culture; the former culture was handled under aerobic circumstances.

Following IB recovery the obtained inclusion body products were subjected to small scale refolding and purification in order to determine the amount of correctly folded insulin precursor protein using HPLC.

The analysis demonstrated that per liter of aerobically processed culture, the yield of the correctly oxidized, folded, and digested insulin precursor amounted only 8.1% as compared to the yield of the culture processed anemically.

Example 2

Figure 2:
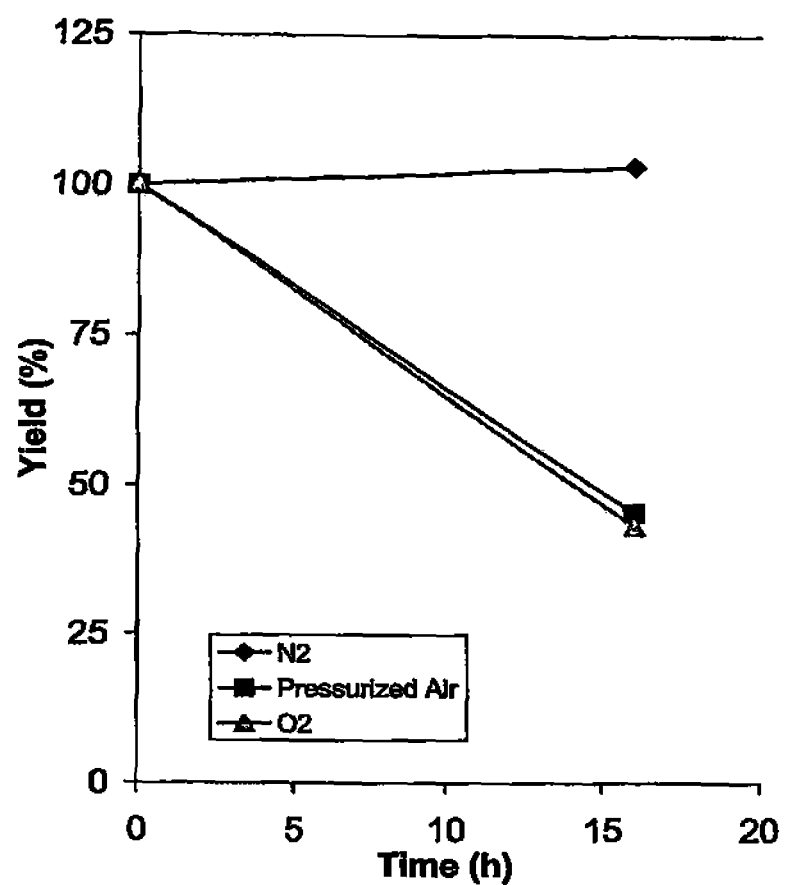
FIG. 2 illustrates the effect of verging of 40 mL aliquots of isolated inclusion body suspensions as described in Example 2.

We were able to demonstrate the effects of different atmosphere conditions on the isolation of insulin peptide. This was done by experiments in which an anoxically recovered suspension of inclusion bodies was dispensed into 8 aliquots of 40 mL. These aliquots were sparged for 16 h. using equal flow rates of nitrogen gas, pressurized air, or oxygen gas, respectively. Next, the suspension and starting material were subjected to small scale refolding and purification to measure the amount of insulin that was obtainable. The analyses showed that sparging the inclusion body suspensions with pressurized air or oxygen gas resulted in sharply reduced yields of correctly folded protein, whereas sparging for 16 h. with nitrogen gas did not have such an effect on the yield. This demonstrates that using the method of the present invention the yield of correctly folded protein can be increased significantly when oxygen is excluded from the insulin precursor inclusion bodies during processing. The results of the experiment are shown in FIG. 2.

The invention claimed is:

1. A method for isolating a recombinant protein that comprises disulfide-bonds in its native conformation, said method comprising the steps of:
   a. maintaining a culture of recombinant prokaryotic host cells containing an expression cassette which directs the expression of the recombinant protein under culture conditions suitable for protein expression;
   b. harvesting and disrupting the prokaryotic host cells thereby producing a crude cell extract and;
   c. isolating the recombinant protein from the cell extract of step b);
   wherein steps b)-c) are performed under essentially anoxic conditions and the recombinant protein recovered in step c) is isolated in its native conformation and biologically active form without the use of reducing agents; and wherein the recombinant protein is present as inclusion bodies in the prokaryotic host cells.

2. The method according to claim 1, wherein the recombinant protein is expressed as a fusion protein.

3. The method according to claim 1, wherein said protein is a precursor protein.

4. The method according to claim 1, wherein said protein is insulin.

5. The method according to claim 1, wherein said essentially anoxic conditions is a nitrogen atmosphere.

* * * * *